United States Patent
Vogel et al.

(10) Patent No.: US 7,753,855 B1
(45) Date of Patent: Jul. 13, 2010

(54) IMPLANTABLE CARDIAC DEVICE PROVIDING SUDDEN CARDIAC DEATH SUSCEPTIBILITY INDICATOR AND METHOD

(75) Inventors: Alan B. Vogel, Saugus, CA (US); Chris Sorensen, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 380 days.

(21) Appl. No.: 11/618,293

(22) Filed: Dec. 29, 2006

(51) Int. Cl.
 *A61B 5/02* (2006.01)
(52) U.S. Cl. ...................................... 600/508
(58) Field of Classification Search ................. 600/508, 600/483, 519, 481; 607/17, 18
See application file for complete search history.

(56) References Cited

U.S. PATENT DOCUMENTS

| | | | |
|---|---|---|---|
| 5,476,483 | A | 12/1995 | Bornzin et al. |
| 6,035,233 | A | 3/2000 | Schroeppel et al. |
| 6,571,121 | B2 | 5/2003 | Schroeppel et al. |
| 6,636,762 | B2 * | 10/2003 | Begemann ................. 600/519 |
| 6,656,125 | B2 | 12/2003 | Misczynski et al. |
| 2003/0023175 | A1 | 1/2003 | Arzbaecher et al. |
| 2004/0215239 | A1 | 10/2004 | Favet et al. |
| 2005/0101873 | A1 | 5/2005 | Misczynski et al. |
| 2007/0249949 | A1 * | 10/2007 | Hadley ........................ 600/519 |

FOREIGN PATENT DOCUMENTS

WO 03045224 A2 6/2003

OTHER PUBLICATIONS

Jouven, Xavier et al., "Heart-Rate Profile During Exercise as a Predictor of Sudden Death," N Engl J Med 2005; 352: 1951-1958.*
Jouven, Xavier MD, Ph.D. et al., "Heart-Rate Profile During Exercise as a Predictor of Sudden Death," N Engl J Med 2005; 352:1951-1958.

* cited by examiner

*Primary Examiner*—George Manuel
*Assistant Examiner*—Robert N Wieland

(57) ABSTRACT

An implantable cardiac stimulation device determines sudden cardiac death susceptibility of a heart. The device comprises a first measuring circuit that measures intrinsic rest rate of the heart, a second measuring circuit that measures heart rate response of the heart and a third measuring circuit that measures heart rate recovery of the heart. The device further comprises a comparator that compares the measured intrinsic rest rate, the measured heart rate response, and the measured heart rate recovery to respective first, second, and third standards and a response circuit that provides a predetermined response when the comparisons of the measured intrinsic rest rate, the measured heart rate response, and the measured heart rate recovery to the respective standards indicate a susceptibility of sudden cardiac death.

12 Claims, 7 Drawing Sheets

IMPLANTABLE CARDIAC DEVICE PROVIDING SUDDEN CARDIAC DEATH SUSCEPTIBILITY INDICATOR AND METHOD

FIELD OF THE INVENTION

The present invention generally relates to an implantable cardiac device. The present invention more particularly relates to such a device capable of indicating a susceptibility of sudden cardiac death and providing a beneficial response thereto.

BACKGROUND OF THE INVENTION

Sudden cardiac death (SCD), or cardiac arrest, is the sudden, abrupt loss of heart function. It is a major health problem, causing about 335,000 deaths each year in the United States. It often occurs instantly or shortly after symptoms appear. The most common cause of SCD is cardiovascular disease, in particular, coronary heart disease. However, SCD may be caused by almost all known heart diseases including degeneration of the heart muscle or cardiac enlargement in patients with congestive heart failure (CHF). Hence, an underlying heart disease is nearly always found in victims of sudden cardiac death. Most cardiac arrests occur when the diseased heart begins to exhibit rapid and/or chaotic activity known as ventricular fibrillation.

Ventricular fibrillation is an immediately life threatening condition. One suffering from ventricular fibrillation must have immediate therapy. Such therapy may be provided by an implantable cardiac stimulation device including an implantable cardiac defibrillator (ICD).

Implantable cardiac devices are well known in the art. They may take the form of implantable defibrillators or cardioverters which treat accelerated rhythms of the heart such as fibrillation or implantable pacemakers which maintain the heart rate above a prescribed limit, such as, for example, to treat a bradycardia. Implantable cardiac devices are also known which incorporate both a pacemaker and a defibrillator (ICD).

A pacemaker may be considered to be comprised of two major components. One component is a pulse generator which generates the pacing stimulation pulses and includes the electronic circuitry and the power cell or battery. The other component is the lead, or leads, having electrodes which electrically couple the pacemaker to the heart. A lead may provide both unipolar and bipolar pacing and/or sensing electrode configurations. In the unipolar configuration, the pacing stimulation pulses are applied or intrinsic responses are sensed between a single electrode carried by the lead, in electrical contact with the desired heart chamber, and the pulse generator case. The electrode serves as the cathode (negative pole) and the case serves as the anode (positive pole). In the bipolar configuration, the pacing stimulation pulses are applied or intrinsic responses are sensed between a pair of closely spaced electrodes carried by the lead, in electrical contact with the desired heart chamber, with the most proximal electrode serving as the anode and the most distal electrode serving as the cathode.

Pacemakers deliver pacing pulses to the heart to induce a depolarization and a mechanical contraction of that chamber when the patient's own intrinsic rhythm fails. To this end, pacemakers include sensing circuits that sense cardiac activity for the detection of intrinsic cardiac events such as intrinsic atrial events (P waves) and intrinsic ventricular events (R waves). By monitoring such P waves and/or R waves, the pacemaker circuits are able to determine the intrinsic rhythm of the heart and provide stimulation pacing pulses that force atrial and/or ventricular depolarizations at appropriate times in the cardiac cycle when required to help stabilize the electrical rhythm and optimize the hemodynamics of the heart.

Pacemakers are described as single-chamber or dual-chamber systems. A single-chamber system stimulates and senses in one chamber of the heart (atrium or ventricle). A dual-chamber system stimulates and/or senses in both chambers of the heart (atrium and ventricle). Dual-chamber systems may typically be programmed to operate in either a dual-chamber mode or a single-chamber mode. Dual chamber represents coordinated atrial and ventricular activity, with the atrial contraction occurring at the appropriate amount of time before the ventricular contraction.

Recently, there has been the introduction of pacing systems that stimulate in corresponding chambers of the heart as, for example, the right ventricle (RV) and left ventricle (LV). These are termed biventricular stimulation devices and may be programmed to operate in single, dual or tri chamber modes. Future designs may include the Left Atrium (LA) and operate in quad chamber modes.

Biventricular pacing has been shown to coordinate contractions of the left and right ventricles, reduce the amount of blood flow that leaks through the mitral valve, and decreases the motion of the septal wall that separates the chambers of the heart. Such motion can affect the quantity of blood that the ventricle can pump out in a single beat. Biventricular pacing has its greatest benefit when optimally timed after the atrial contraction, and the right ventricular and left ventricular contractions are also optimally timed.

Biventricular pacing has been found to be particularly advantageous in patient's suffering from congestive heart disease because of the improved ability of the left ventricle to fully pump blood from the heart. As a result, patients are able to tolerate greater exertion, have a longer life span, and experience a higher quality of life.

Implantable cardiac defibrillators (ICD's) as previously mentioned may be incorporated with a pacemaker. They are generally electrically connected to the heart with one or more defibrillation electrodes of the lead system. One defibrillator electrode may be the conductive housing of the device. A lead of the lead system may include at least one other defibrillation electrode arranged to be positioned in the right ventricle. An arrhythmia detector detects ventricular arrhythmias, such as ventricular fibrillation. When such an arrhythmia is detected, a pulse generator delivers a defibrillating shock between the defibrillation electrode in the right ventricle and the conductive housing to terminate the fibrillation. Alternatively, the lead system of such defibrillation devices may further include another defibrillation electrode arranged to be positioned in the right atrium or superior vena cava (SVC), hereinafter referred to as the SVC electrode, which may be electrically connected to the right ventricular defibrillation electrode. In this arrangement, the defibrillating shock is delivered between the commonly connected right ventricular and SVC electrodes and the conductive housing.

As previously mentioned, ventricular fibrillation is an immediately life threatening cardiac arrhythmia. It requires immediate and effective defibrillation therapy. As a result, an ICD must be capable of providing a defibrillation shock having an output magnitude that is above the output level that is required to defibrillate the fibrillating heart chamber. This is known as the defibrillation threshold (DFT).

Since many patients at risk of SCD have an implanted cardiac stimulation device, it would be most appropriate if the device could provide some indication of SCD susceptibility. This may then be followed by notification of the susceptibility and/or a response to provide more appropriate pacing therapy and/or trending of SCD susceptibility metrics for further analysis of the patient's condition. The present invention addresses these issues.

SUMMARY OF THE INVENTION

There is described an implantable cardiac stimulation device that determines sudden cardiac death susceptibility of a heart. The device comprises a first measuring circuit that measures intrinsic rest rate of the heart, a second measuring circuit that measures heart rate response of the heart, and a third measuring circuit that measures heart rate recovery of the heart. The device further comprises a comparator that compares the measured intrinsic rest rate, the measured heart rate response, and the measured heart rate recovery to respective first, second, and third standards, and a response circuit that provides a predetermined response when the comparisons of the measured intrinsic rest rate, the measured heart rate response, and the measured heart rate recovery to the respective standards indicate a susceptibility of sudden cardiac death.

The first standard may be a fixed standard, such as a heart rate and the second and third standards may be dynamic standards, such as a rate of change. For example, the device may further comprise an activity sensor that provides a sensor indicated rate and the second standard may be a rate of change of the sensor indicated rate. A measured heart rate response that is less than the second standard may be considered indicative of susceptibility of sudden cardiac death.

Similarly, the third standard may also be a rate of change of the sensor indicated rate. A measured heart rate recovery that is less than the third standard may also be considered indicative of susceptibility of sudden cardiac death.

The device may be operative responsive to programmed parameters. The response circuit may include a parameter adjusting circuit that adjusts the programmed parameters when the comparisons of the measured intrinsic rest rate, the measured heart rate response, and the measured heart rate recovery to the respective standards indicate a susceptibility of sudden cardiac death.

The response circuit may alternatively or in addition comprise a trending circuit. The trend circuit may trend at least one metric of heart performance when the comparisons of the measured intrinsic rest rate, the measured heart rate response, and the measured heart rate recovery to the respective standards indicate a susceptibility of sudden cardiac death.

The response circuit may comprise a notifier circuit. The notifier circuit may be a patient notifier and/or an indicator to the clinician. It may provide a perceptible notification of susceptibility of cardiac death when the comparisons of the measured intrinsic rest rate, the measured heart rate response, and the measured heart rate recovery to the respective standards indicate a susceptibility of sudden cardiac death.

In another embodiment, an implantable cardiac stimulation device determines sudden cardiac death susceptibility of a heart. The device comprises a first measuring circuit that measures intrinsic rest rate of the heart, a second measuring circuit that measures heart rate response of the heart, and a third measuring circuit that measures heart rate recovery of the heart. The device further comprises a comparator that compares the measured intrinsic rest rate, the measured heart rate response, and the measured heart rate recovery to respective first, second, and third standards and sets a first flag when the measured intrinsic rest rate is above the first standard, a second flag when the measured heart rate response is below the second standard, and a third flag when the measured heart rate recovery is below the third standard, and a response circuit that provides a predetermined response when the comparisons of the measured intrinsic rest rate, the measured heart rate response, and the measured heart rate recovery to the respective standards cause the comparator to concurrently set the first, second, and third flags to indicate a susceptibility of sudden cardiac death.

In another embodiment, a method that determines sudden cardiac death susceptibility of a heart for use in an implantable cardiac stimulation device comprises the steps of measuring intrinsic rest rate of the heart, measuring heart rate response of the heart, and measuring heart rate recovery of the heart. The method further comprises comparing the measured intrinsic rest rate, the measured heart rate response, and the measured heart rate recovery to respective first, second, and third standards and providing a predetermined response when the comparisons of the measured intrinsic rest rate, the measured heart rate response, and the measured heart rate recovery to the respective standards indicate a susceptibility of sudden cardiac death.

BRIEF DESCRIPTION OF THE DRAWINGS

Further features and advantages of the present invention may be more readily understood by reference to the following description taken in conjunction with the accompanying drawings, in which.

DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
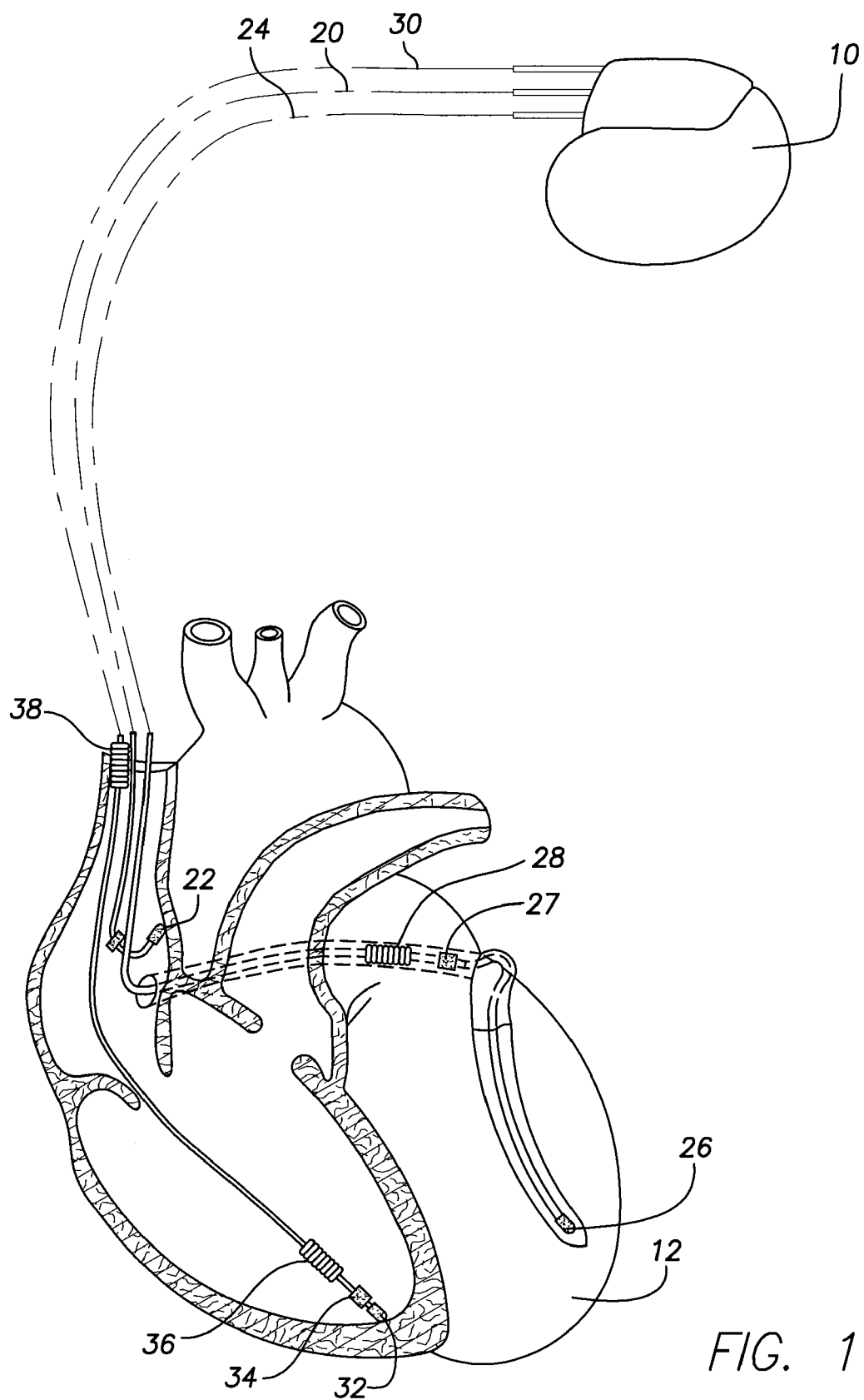
FIG. 1 is a simplified diagram illustrating an implantable stimulation device embodying the present invention in electrical communication with at least three leads implanted into a patient's heart for delivering multi-chamber stimulation and shock therapy.

As shown in FIG. 1, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus ostium for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
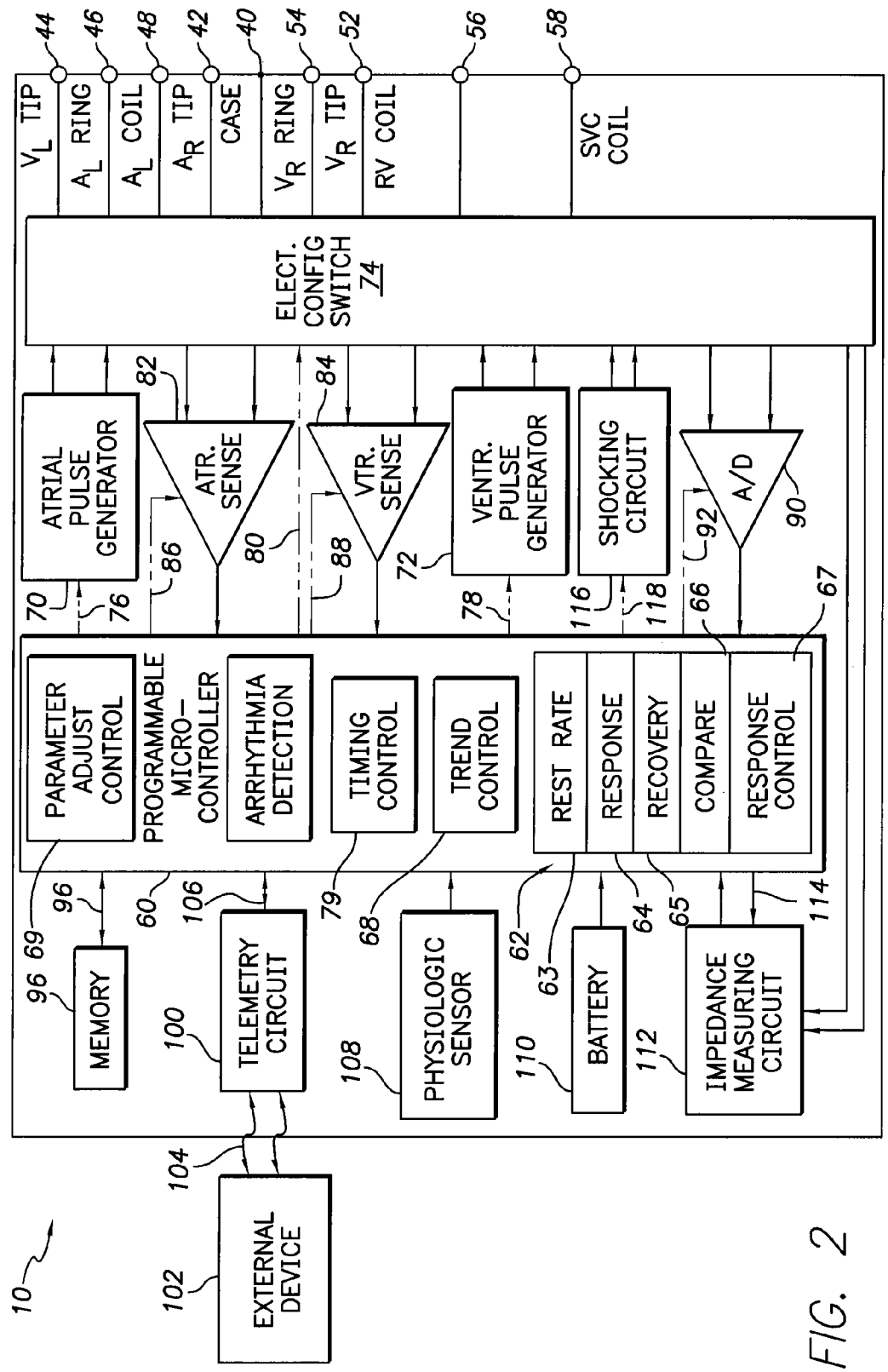
FIG. 2 is a functional block diagram of the device of FIG. 1 illustrating the basic elements thereof which can provide cardioversion, defibrillation and pacing stimulation in four chambers of the heart.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to provide a physiologic sensor indicated rate signal to adjust pacing stimulation rate according to the exercise state of the patient. However, the physiological sensor 108 may further be used to detect changes in cardiac output, changes in the physiological condition of the heart, or indicate diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses.

In one embodiment of the present invention, the physiologic sensor is further utilized to enable detection of rest state of the patient. The rest state detector may employ a sensor, known as an "activity variance" sensor wherein an activity is monitored to detect a low variance in the measurement corresponding to the rest state. For a complete description of the activity variance sensor, see U.S. Pat. No. 5,476,483 (Bornzin et. al), issued Dec. 19, 1995, which patent is hereby incorporated by reference.

The stimulation device additionally includes a battery 110 which provides operating power to all of the circuits shown in FIG. 2. For the stimulation device 10, which employs shocking therapy, the battery 110 must be capable of operating at low current drains for long periods of time and then be capable of providing high-current pulses (for capacitor charging) when the patient requires a shock pulse. The battery 110 must also have a predictable discharge characteristic so that elective replacement time can be detected. Accordingly, the device 10 may employ lithium/silver vanadium oxide batteries, as are known in the art.

As further shown in FIG. 2, the device 10 is shown as having an impedance measuring circuit 112 which is enabled by the microcontroller 60 via a control signal 114. The known uses for an impedance measuring circuit 120 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 120 is advantageously coupled to the switch 74 so that any desired electrode may be used.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5-10 joules), or high energy (11 to 40 joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

With continued reference to FIG. 2, and in accordance with this embodiment, the device 10 further includes a SCD susceptibility indicator circuit 62. The SCD susceptibility indicator circuit 62 includes a rest rate measuring circuit 63, a heart rate response measuring circuit 64, a heart rate recovery measuring circuit 65, a comparator circuit 66, and a response control circuit 67.

In accordance with this embodiment, SCD susceptibility is indicated when a rest rate flag, a heart rate response flag, and a heart rate recovery flag are set concurrently. This requires all three of these metrics of SCD susceptibility to be measured and compared to respective first, second, and third standards. To that end, the circuit 63 measures the resting intrinsic heart rate of the patient. It makes use of the activity variance derived from the physiologic sensor 108 to make sure the patient is at rest before it measures the patient's heart rate. It will also make sure that the heart has not received any pacing pulses for a time before the resting intrinsic heart rate is measured. Once the resting intrinsic heart rate is measured, the comparator circuit 66 compares the measured resting heart rate to a fixed, predetermined heart rate of, for example, seventy-five beats per minute (bpm). If the measured resting heart rate is greater than the fixed first standard of seventy-five bpm, that is considered indicative of SCD susceptibility and a resting heart rate flag is set.

The circuit 64 measures heart rate response. Here, when the patient becomes active, the circuit measures the responding heart rate while sensor driven pacing is disabled. It then uses the comparator to compare the measured responding heart rate to the current activity based sensor indicated rate (second standard) derived from the physiologic sensor 108. This is graphically illustrated in FIG. 3. Here it may be seen that the response period is P1 and that the activity based sensor indicated rate 120 during the response period P1 is greater than the measured responding heart rate 122. This indicates a sluggish heart rate response and causes the comparator 66 to set a heart rate response flag, also indicative of SCD susceptibility.

Similarly, the circuit 65 measures heart rate recovery. Here, when the patient becomes less active, the circuit measures the recovery heart rate. It then uses the comparator to compare the measured recovering heart rate to the current activity based sensor indicated rate (third standard) derived from the physiologic sensor 108. This is graphically illustrated in FIG. 4. Here it may be seen that the recovery period is P2 and that the activity based sensor indicated rate 120 during the recovery period P2 is less than the measured recovering heart rate 124. This indicates a sluggish heart rate recovery and causes the comparator 66 to set a heart rate recovery flag, further indicative of SCD susceptibility.

When all three flags are concurrently set, SCD susceptibility is indicated. This causes the response control to formulate a predetermined response to the SCD susceptibility indication. The response may be preprogrammed into the device 10.

The response may take the form of notification, and/or heart performance trending, and/or programmed parameter adjustment. To that end, the device may employ the telemetry circuit 100 to transmit a SCD susceptibility notice to a non-implanted receiver, such as external programmer 102 during a next follow-up visit to the patient's physician.

The device may employ a trend control 68 to cause one or more metrics of heart performance related to SCD susceptibility to be trended for later more detailed analysis. Such metrics may include, for example, resting heart rate, heart rate response and recovery, or pacing and sensing thresholds, ventricular pressure, atrial pressure, stroke volume, transthoracic impedance, $SVO_2$, or transcardiac impedance. Such metrics and methods for measuring the same are well known in the art.

The device may further employ a parameter adjust control 69 to adjust one or more device pacing parameters to more effectively respond to the heart condition precipitating the SCD susceptibility indication. Parameters that may be adjusted may include, for example, pacing mode, pacing rate, the rate of change in the pacing rate, the AV delay, the interventricular (V-V) interval, or the maximum sensor rate.

Figure 5:
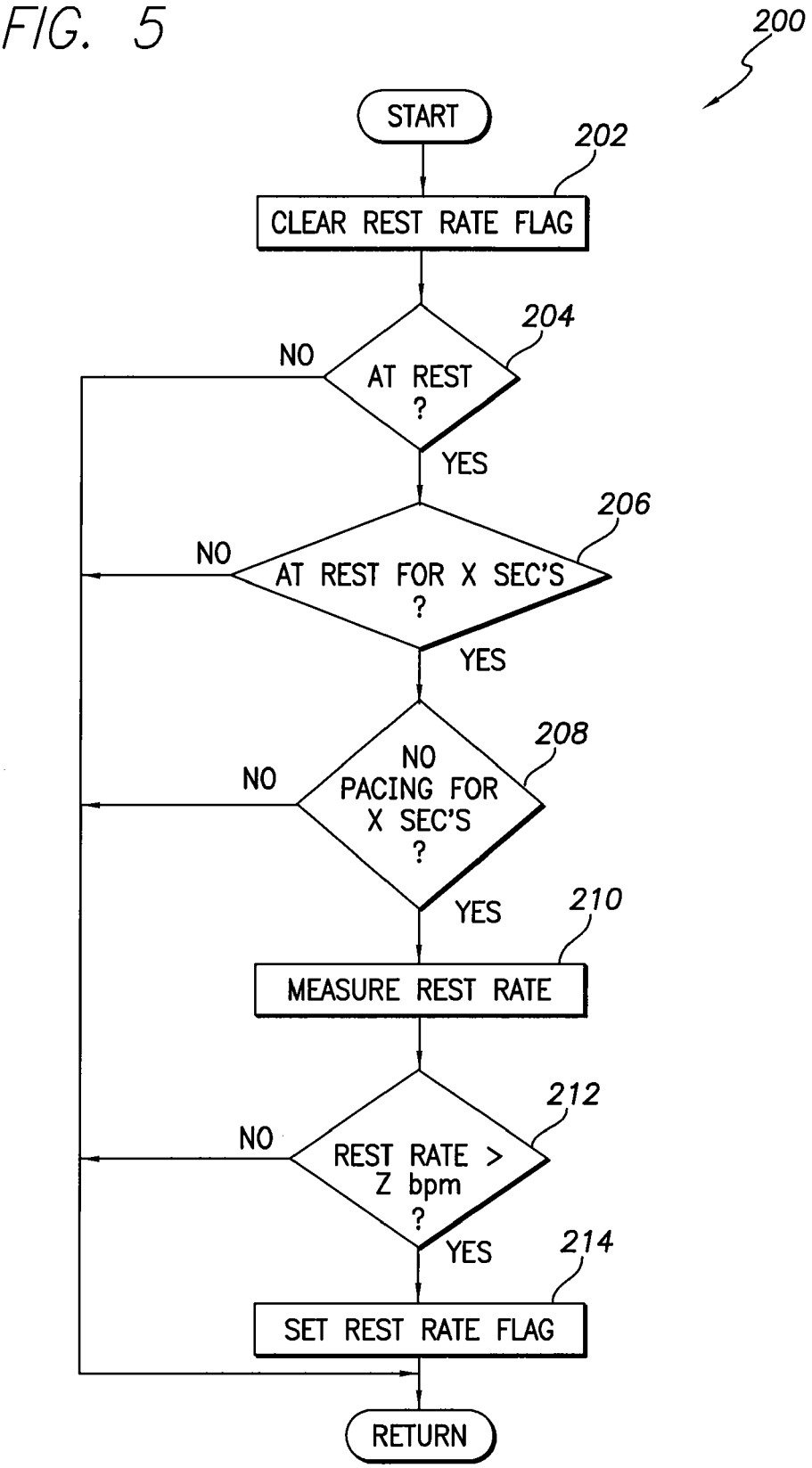
FIG. 5 is a flow diagram describing the manner in which a resting heart rate flag may be set according to one embodiment of the invention.

In FIG. 5, a flow chart is shown describing a manner in which the resting intrinsic heart rate flag may be set in one embodiment of the device 10. In this flow chart, and the other flow charts described herein, the various algorithmic steps are summarized in individual "blocks". Such blocks describe specific actions or decisions that must be made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

The process 200 of FIG. 5 initiates with activity block 202 where the resting heart rate flag, if previously set, is cleared. Next, in decision block 204, the resting heart rate measuring circuit 63 checks to determine if the patient is now at rest. This my be accomplished by making use of the activity variance as previously described. If the patient is not at rest, the process returns. However if the patient is at rest, the process proceeds to decision block 206 to determine if the patient has been at rest for X seconds where, X is of sufficient time to assure a valid resting heart rate measurement. To that end, X may be one minute (60 seconds), for example, but may be selectively chosen depending on the individual patient's needs. The time at rest may be kept by the timing control 79. If the patient has not been at rest for X seconds, the process returns.

If the patient has been at rest for X seconds, the process advances to decision block 208 wherein it is determined if the patient has also not been paced for X seconds. This step is performed because it is desired to measure a true intrinsic resting heart rate. If the patient has been paced within the last X seconds, the process returns. However, if the patient has also not been paced for X seconds, the process advances to activity block 210 where the intrinsic resting heart rate is measured.

The process then advances to decision block 212 wherein the comparator 66 compares the measured intrinsic resting heart rate to the first standard of, for example, seventy-five bpm. If the resting intrinsic heart rate is below the first standard, the process returns. However, if the resting intrinsic heart rate is above the first standard, the process proceeds to activity block 214 wherein the resting intrinsic heart rate flag is set. The process then returns.

Figure 6:
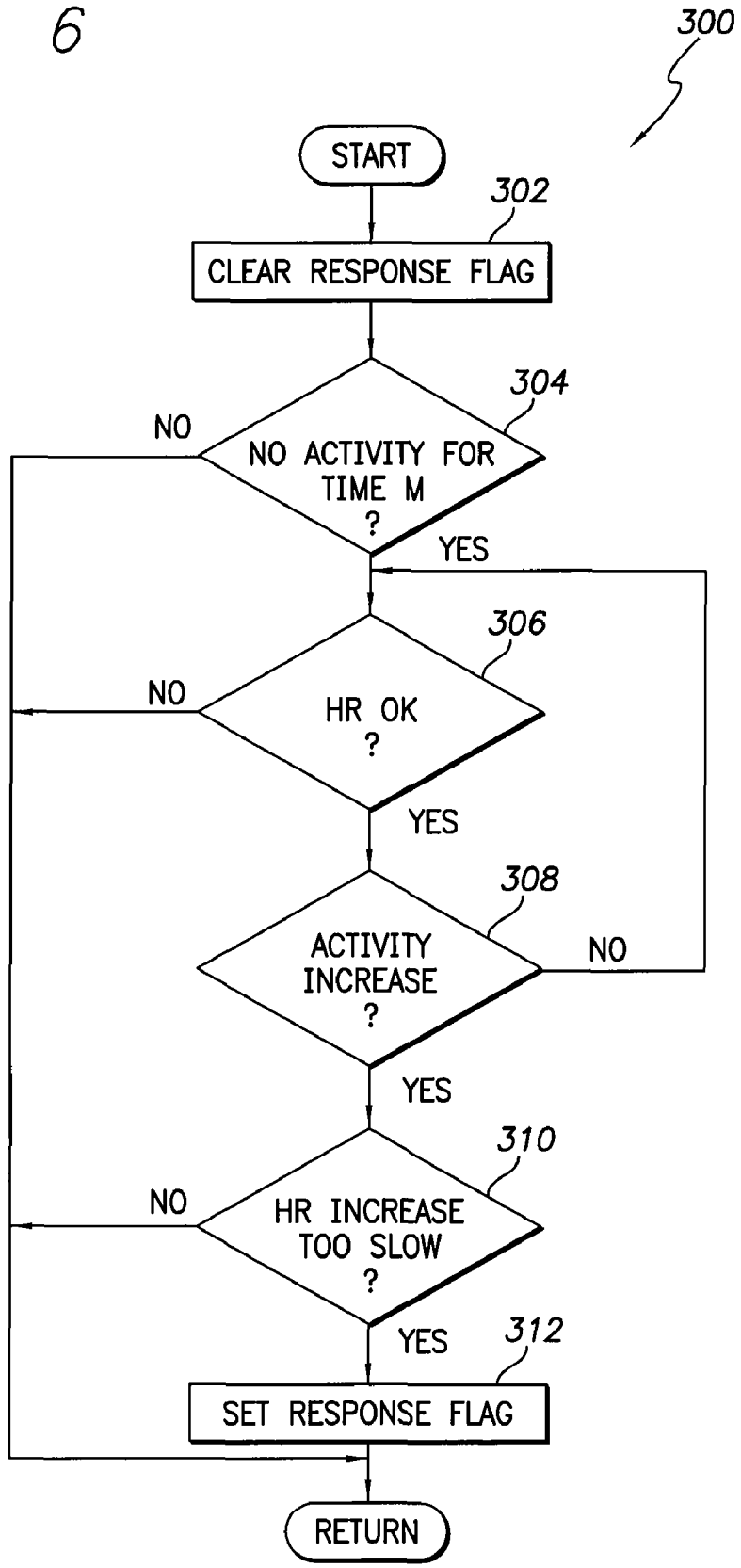
FIG. 6 is a flow diagram describing the manner in which a heart rate response flag may be set according to one embodiment of the invention.

FIG. 6 shows a manner in which a heart rate response flag may be set in an embodiment of the invention. The process 300 of FIG. 6 initiates with activity block 302 wherein the heart rate response flag is cleared if previously set. Then, the process advances to decision block 304 wherein it is determined if the patient has been inactive for time M. Again, the activity variance and timing control 79 may be employed for this purpose. If the patient has not been inactive for time M, the process returns. However, if the patient has been inactive for time M, which may be on the order of five minutes, for example, the process advances to decision block 306 wherein it is determined if the patient's heart rate is appropriate for the patient's inactivity. If not, the process returns. However, if the patient's heart rate is appropriate for the patient's inactivity, which may be determined by comparator 66 comparing the patient's current heart rate to the sensor indicated rate, the process advances to decision block 308.

Figure 3:
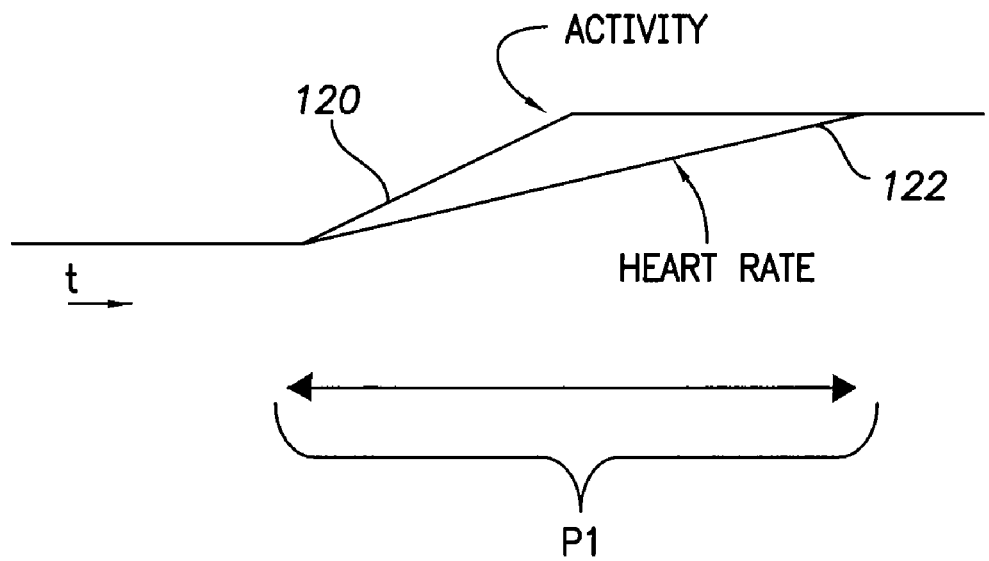
FIG. 3 is a graphical illustration of a sluggish heart rate response.

In decision block 308, it is determined if there is now an increase in the patient's activity. If not, the process returns to decision block 306. If there is an increase in the patient's activity, the process advances to decision block 310. Here, the comparator 66 compares the responding heart rate to the sensor indicated rate during the time period P1 as shown in FIG. 3. If the responding heart rate is below the sensor indicated rate, indicating a sluggish heart rate response, the process advances to activity block 312 where the response flag is set. The process then returns.

Figure 7:
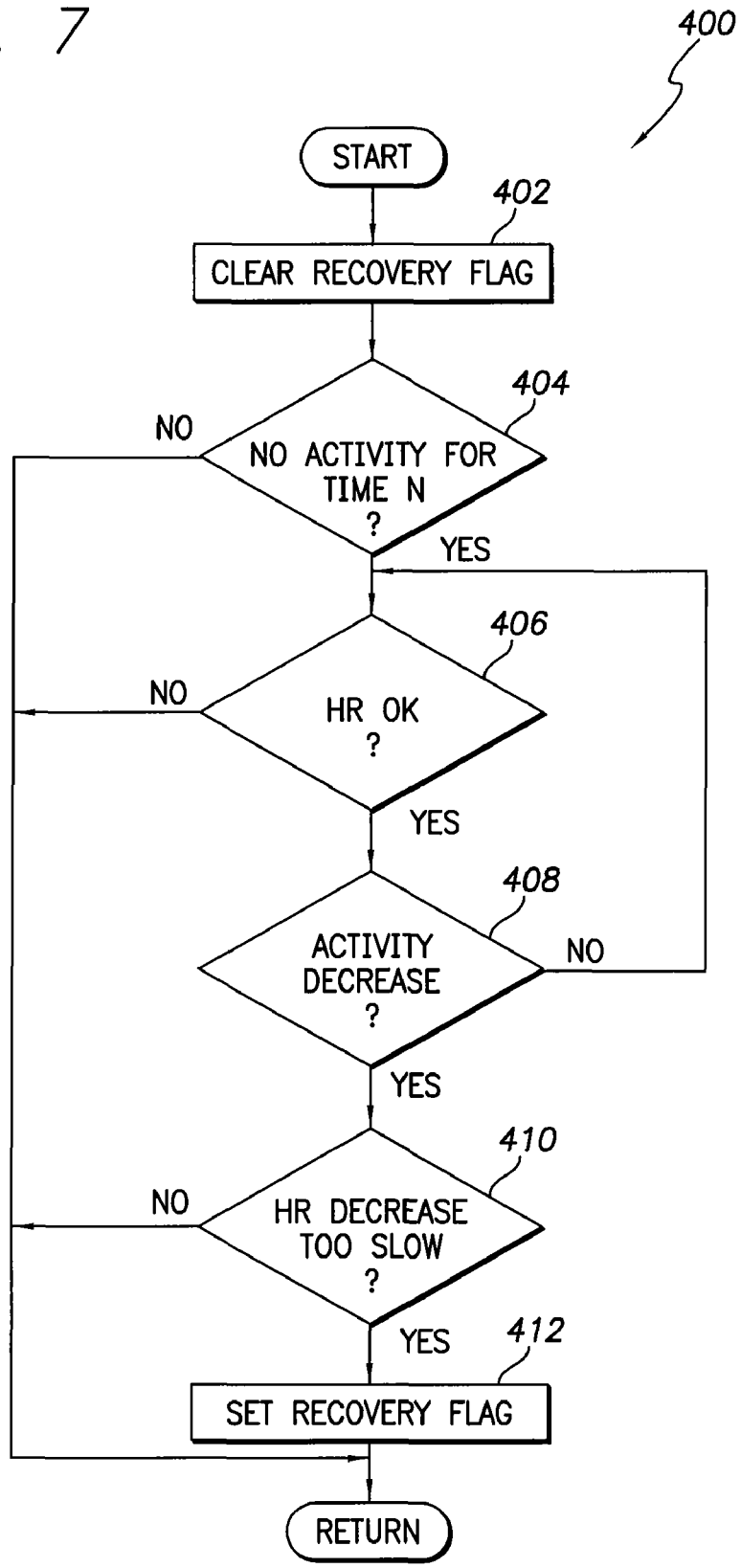
FIG. 7 is a flow diagram describing the manner in which a heart rate recovery flag may be set according to one embodiment of the invention.

FIG. 7 shows a similar manner in which a heart rate recovery flag may be set in an embodiment of the invention. The process 400 of FIG. 7 initiates with activity block 402 wherein the heart rate recovery flag is cleared if previously set. Then, the process advances to decision block 404 wherein it is determined if the patient has been active for time N. Again, the activity variance and timing control 79 may be employed for this purpose. If the patient has not been active for time N, the process returns. However, if the patient has been active for time N, which may be on the order of five minutes, for example, the process advances to decision block 406 wherein it is determined if the patient's heart rate is appropriate for the patient's activity. If not, the process returns. However, if the patient's heart rate is appropriate for the patient's activity, which may be determined by comparator 66 comparing the patient's current heart rate to the sensor indicated rate, the process advances to decision block 408.

Figure 4:
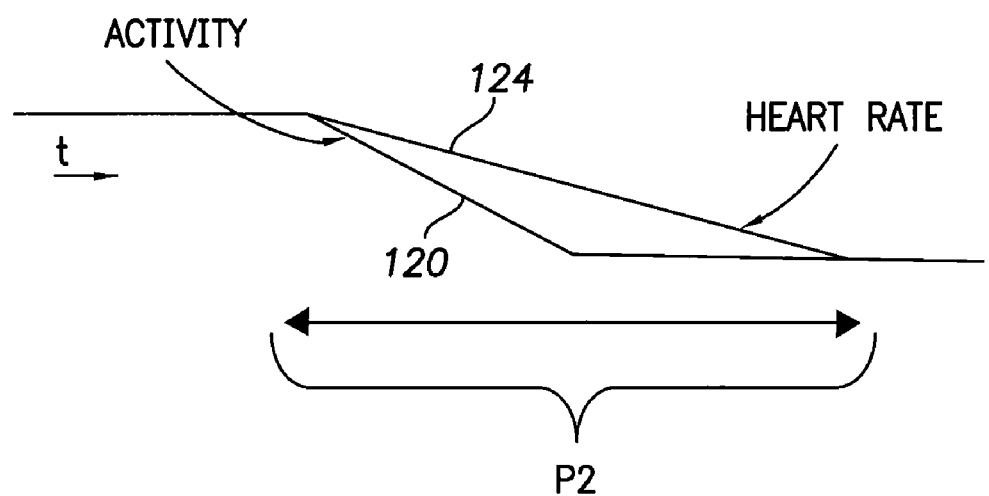
FIG. 4 is a graphical illustration of a sluggish heart rate recovery.

In decision block 408, it is determined if there is now a decrease in the patients activity. If not, the process returns to decision block 306. If there is a decrease in the patient's activity, the process advances to decision block 410. Here, the comparator 66 compares the recovering heart rate to the sensor indicated rate during the time period P2 as shown in FIG. 4. If the recovering heart rate is above the sensor indicated rate, indicating a sluggish heart rate recovery, the process advances to activity block 412 where the recovery flag is set. The process then returns.

Figure 8:
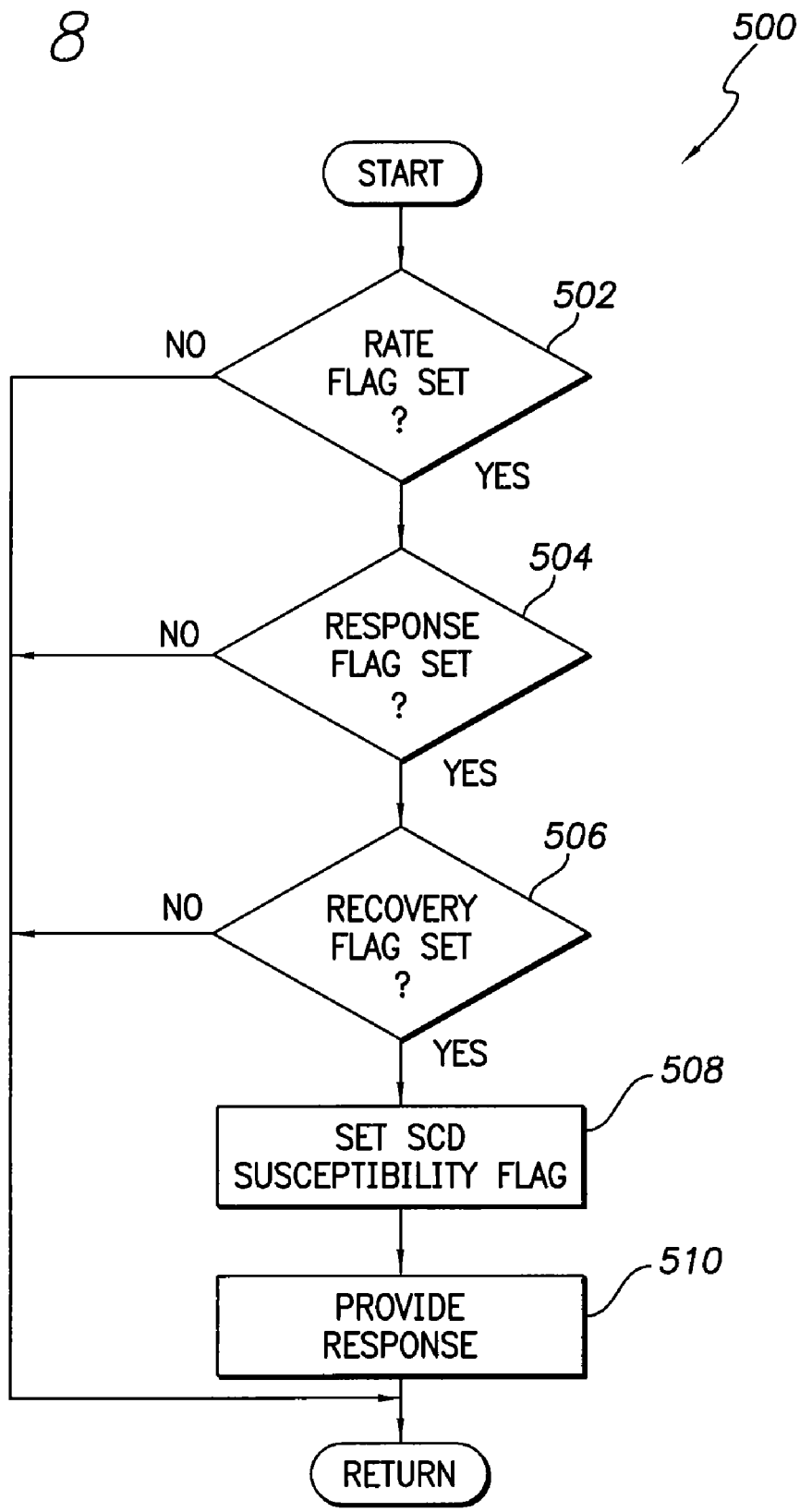
FIG. 8 is a flow diagram describing the manner in which SCD susceptibility may be indicated responsive to the setting of a resting heart rate flag, a heart rate response flag, and a heart rate recovery flag according to one embodiment of the invention.

Referring now to FIG. 8, it shows a flow diagram describing the manner in which SCD susceptibility may be indicated responsive to the setting of a resting heart rate flag, a heart rate response flag, and a heart rate recovery flag according to one embodiment of the invention. The process 500 of FIG. 8 initiates with decision block 502. Here it is determined if the resting intrinsic heart rate flag has been set. If it has not, the process returns. However, if the resting intrinsic heart rate flag has been set, the process advances to decision block 504. Here it is determined if the heart rate response flag has been set. If it has not, the process returns. However, if heart rate response flag has been set, the process advances to decision block 506. Here it is determined if the heart rate recovery flag has been set. If it has not, the process returns. However, if heart rate recovery flag has been set, the process advances to activity block 508.

In activity block 508, because all three flags are concurrently set, the SCD susceptibility flag is set. The process then advances to activity block 510 wherein, in response to the SCD susceptibility flag being set, the response control 67 initiates a predetermined response. Any one all of the SCD susceptibility responses previously described may be initiated. The process then returns.

While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

What is claimed is:

1. An implantable cardiac stimulation device that determines sudden cardiac death susceptibility of a heart, comprising:
   a first measuring circuit that measures intrinsic rest rate of the heart;
   a second measuring circuit that measures heart rate response of the heart to an increase in activity level;
   a third measuring circuit that measures heart rate recovery of the heart in response to a reduction of activity level;
   a memory for storing an intrinsic rest rate standard;
   a hemodynamic sensor adapted to provide a sensor indicated heart rate as a function of activity level;
   a controller adapted to determine a rate of change of the sensor indicated heart rate;
   a comparator that compares the measured intrinsic rest rate to the intrinsic rest rate standard, the measured heart rate response to a first rate of change of the sensor indicated heart rate, and the measured heart rate recovery to a second rate of change of the sensor indicated heart rate; and
   a response circuit that provides a predetermined response when the comparisons of the measured intrinsic rest rate, the measured heart rate response, and the measured heart rate recovery to indicate a susceptibility of sudden cardiac death.

2. The device of claim 1 wherein the physiologic sensor comprises an activity sensor that provides the sensor indicated rate.

3. The device of claim 2, wherein a measured heart rate response that is less than the first rate of change of the sensor indicated rate is indicative of susceptibility of sudden cardiac death.

4. The device of claim 2, wherein a measured heart rate recovery that is less than the second rate of change of the sensor indicated rate is indicative of susceptibility of sudden cardiac death.

5. The device of claim 1, wherein the device is operative responsive to programmed parameters, and wherein the response circuit includes a parameter adjusting circuit that adjusts the programmed parameters when the comparisons of the measured intrinsic rest rate, the measured heart rate response, and the measured heart rate recovery to the respective standards indicate a susceptibility of sudden cardiac death.

6. The device of claim 1, wherein the response circuit comprises a trending circuit that trends at least one metric of heart performance when the comparisons of the measured intrinsic rest rate, the measured heart rate response, and the measured heart rate recovery to the respective standards indicate a susceptibility of sudden cardiac death.

7. The device of claim 1, wherein the response circuit comprises a notifier circuit that provides a perceptible notification of susceptibility of cardiac death when the comparisons of the measured intrinsic rest rate, the measured heart rate response, and the measured heart rate recovery to the respective standards indicate a susceptibility of sudden cardiac death.

8. In an implantable cardiac stimulation device, a method that determines sudden cardiac death susceptibility of a heart, comprising:

measuring intrinsic rest rate of the heart;

measuring heart rate response of the heart to an increase in activity level;

measuring heart rate recovery of the heart in response to a decrease in activity level;

determining with a physiologic sensor a sensor indicated heart rate as a function of activity level;

comparing the measured intrinsic rest rate to a intrinsic rest rate threshold, the measured heart rate response to a first rate of change of the sensor indicated heart rate, and the measured heart rate recovery to a second rate of change of the sensor indicated heart rate; and providing a predetermined response when the comparisons of the measured intrinsic rest rate, the measured heart rate response, and the measured heart rate recovery indicate a susceptibility of sudden cardiac death.

9. The method of claim 8, wherein the device is operative responsive to programmed parameters, and wherein the predetermined response includes adjusting the programmed parameters when the comparisons of the measured intrinsic rest rate, the measured heart rate response, and the measured heart rate recovery indicate a susceptibility of sudden cardiac death.

10. The method of claim 8, wherein the predetermined response includes trending at least one metric of heart performance when the comparisons of the measured intrinsic rest rate, the measured heart rate response, and the measured heart rate recovery indicate a susceptibility of sudden cardiac death.

11. The method of claim 8, wherein the predetermined response includes providing a perceptible notification of susceptibility of cardiac death when the comparisons of the measured intrinsic rest rate, the measured heart rate response, and the measured heart rate recovery indicate a susceptibility of sudden cardiac death.

12. The method of claim 8 comprising the further steps of setting a first flag when the measured intrinsic rest rate is above the intrinsic rest rate threshold, setting a second flag when the measured heart rate response is below the first rate of change of a sensor indicated heart rate, and setting a third flag when the measured heart rate recovery is below second rate of change of a sensor indicated heart rate, and wherein the providing step is performed when the first flag, the second flag, and third flag are concurrently set.

* * * * *